United States Patent [19]
Hill

[11] Patent Number: 5,529,063
[45] Date of Patent: Jun. 25, 1996

[54] MODULAR SYSTEM FOR CONTROLLING THE FUNCTION OF A MEDICAL ELECTRONIC DEVICE

[75] Inventor: Douglas J. Hill, Renton, Wash.

[73] Assignee: Physio-Control Corporation, Redmond, Wash.

[21] Appl. No.: 207,869

[22] Filed: Mar. 8, 1994

[51] Int. Cl.⁶ ................................. A61B 5/00; A61B 8/06
[52] U.S. Cl. .................. 128/630; 128/653.10; 128/760; 174/52.10; 361/683
[58] Field of Search ..................................... 128/630, 670, 128/671, 695, 696, 710, 760, 653.1; 174/50.52, 52.1, 58, 59, 61; 206/521, 404; 439/371; 361/383

[56] References Cited

U.S. PATENT DOCUMENTS

| | | | |
|---|---|---|---|
| 2,970,243 | 1/1961 | Riesz et al. | 174/52.1 |
| 3,865,101 | 2/1975 | Saper et al. | 128/2.06 R |
| 4,082,084 | 4/1978 | Lipscher | 128/2 D |
| 4,919,619 | 4/1990 | Chompff | 439/371 |
| 4,981,144 | 1/1991 | Carels, Jr. | 128/760 |
| 5,323,291 | 6/1994 | Boyle et al. | 361/683 |
| 5,360,005 | 11/1994 | Wilk | 128/653.1 |

*Primary Examiner*—Angela D. Sykes
*Assistant Examiner*—Stephen Huang
*Attorney, Agent, or Firm*—Seed and Berry

[57] ABSTRACT

A medical electronic device having an electronic circuit allows for additional functional modules having electrical components to electrically couple to the medical electronic circuit. The modular system includes a housing enclosing the medical electronic circuit and a module enclosing the electrical components containing the additional functionality. A socket for releasably receiving the module is formed in a top side of the housing and is defined by a bottom wall and a side wall of the housing. The side wall has a rib projecting therefrom and extending from the bottom wall toward the top of the housing. The bottom wall has first and second holes formed therein proximate to the first rib. The module includes front and rear sides each having a channel formed therein for receiving the rib. A pair of guide pins extend below the bottom of the case, on opposing sides of an electrical connector. When the module is inserted into the socket, the channels receive the rib, the pair of pins are received by the pair of holes and the electrical connector on the case electrically couples with an electrical connector extending upward from the bottom wall of the socket.

12 Claims, 4 Drawing Sheets

MODULAR SYSTEM FOR CONTROLLING THE FUNCTION OF A MEDICAL ELECTRONIC DEVICE

TECHNICAL FIELD

The present invention relates to medical electronic devices that accept electronic modules to expand or alter the functionality of the medical electronic device.

BACKGROUND OF THE INVENTION

The functions performed by some currently available medical electronic devices can be altered or controlled by accepting various electronic modules that electrically interconnect with the electronic device. For example, heart rate monitors may be expanded to provide blood pressure data upon addition of an appropriate blood pressure monitoring module. Designing such modules to provide upgradability of the medical electronic device is not particularly problematic with stationary devices. When medical electronic devices are designed to be portable, however, problems arise. For example, the portable medical device must generally be compact and lightweight to allow it to be readily portable. As a result, any modules for the portable medical device must also, be compact and lightweight.

In a medical electronic device accepting plug-in modules to control its functions,, it is generally desirable to make the modules quick and easy to install and remove from the electronic device so that the functions performed by the medical device can be easily changed. However, making the module so that it is easily removable has a tendency to make the module easily dislodged by impact shocks. This problem is normally not too serious for stationary medical electronic devices. However, portable electronic: devices are often handled roughly or dropped during active use. If the portable medical electronic device is to accept electronic modules, these modules must be securely retained by the electronic device. Any impact shock that the medical electronic: device may receive must not dislodge or disconnect the electronic module from the device.

One approach to solving this impact shock problem would be for the module to tightly fit into the medical electronic device so that it is not able to move when subjected to impact shocks. However, to prevent the module from electrically disconnecting from the electronic device when subjected to impact shock, close, tight tolerances between the module and a bay in the electronic device accepting the module are generally necessary. These tight tolerances generally cannot be achieved using relatively inexpensive, high volume production techniques. As a result, plug-in modules for portable electronic devices would be relatively expensive.

If the portable electronic device is to be used outdoors or in a variety of environmental conditions, the device must be environmentally sound. It must generally be able to resist penetration of moisture or other fluids into the electronics of the device. Most modular systems provide bays or ports which receive the modules. These bays are generally not environmentally sound because water may easily penetrate through ports in these bays into the interior of the electronic device. To maintain environmental integrity, conventional medical electronic devices that are designed to be portable must eliminate the bay and allow upgradability only internal to the device. Namely, the electronic device must be partially disassembled, the new electronics coupled to the internal electronics in the device, and then the electronic device must be reassembled. This assembly/disassembly does not permit simple upgradability by an average user of the device through the use of a module. Consequently, current portable medical electronic devices that are environmentally sound may not be upgradable through the use of modules.

Overall, no portable medical electronic device of which the inventors are aware avoids impact shock and other environmental hazards inherent in a portable device and yet allows the function of the device to be readily changed or upgraded through the use of easily installed modules.

SUMMARY OF THE INVENTION

According to principles of the present invention, a portable medical electronic device having an electronic circuit allows for additional "feature" modules having electrical components to electrically couple to the medical electronic circuit. The modular system includes a housing enclosing the medical electronic circuit and a module enclosing the electrical components containing the additional features or functionality. The housing has top, bottom, front and rear sides. A socket for receiving the module is formed in the top side of the housing and is defined by a bottom wall and a sidewall of the housing. The sidewall has a first rib projecting therefrom, the first rib extending from the bottom wall to the top of the housing. The bottom wall has first and second holes formed therein proximate to the first rib.

A first electrical connector is electrically coupled to the medical electronic circuit within the housing. The first electrical connector is positioned within the bottom wall of the housing and is retained by the housing between the first and second holes.

The module includes a case having top, bottom, front and rear sides. The front and rear sides of the case each have a channel formed therein extending from the bottom of the case to the top of the case. A second electrical connector projects below the bottom of the case a first distance proximate to the front side of the case. The second electrical connector is electrically coupled to the electrical components in the case. A pair of guide pins extends below the bottom of the case a second distance, proximate to, and on opposing sides of, the second electrical connector. The second distance of the pins is greater than the first distance to thereby protect the second electrical connector if the module were dropped.

The module further includes a latch member extending from the front side of the case, proximate to the top of the case. The latch member is for movement between an extended latched position and a retracted unlatched position. An actuator assembly retained by the case is adapted to move the latch member between the extended latched position and the retracted unlatched position. The housing includes a ledge extending along an upper portion of the sidewall, transverse to the first rib. The ledge projects into the housing and is positioned to receive the latch member when the module is inserted into the socket and when the latch member is in the extended latch position. When so inserted, the second electrical connector of the module electrically couples with the first electrical connector at the bottom wall of the socket in the housing.

The present invention solves problems inherent in the prior art by providing a compact module that may readily and electrically couple to a portable medical electronic device. The module includes circuitry that provides additional function features to the medical electronic device. The socket in the housing of the medical electronic device is sealed from the medical electronic circuitry within the housing to thereby provide environmental integrity for the device. The actuator assembly and latch member allow the modules to be readily inserted and removed from the socket. The interplay of tolerances between the ribs and channels, and pins and holes, also allows the modules to be readily inserted into the socket of the medical electronic device. Other features and advantages of the present invention will become apparent from studying the following detailed description of the presently preferred exemplary embodiment, together with the following drawings.

DETAILED DESCRIPTION OF THE INVENTION

Figure 1:
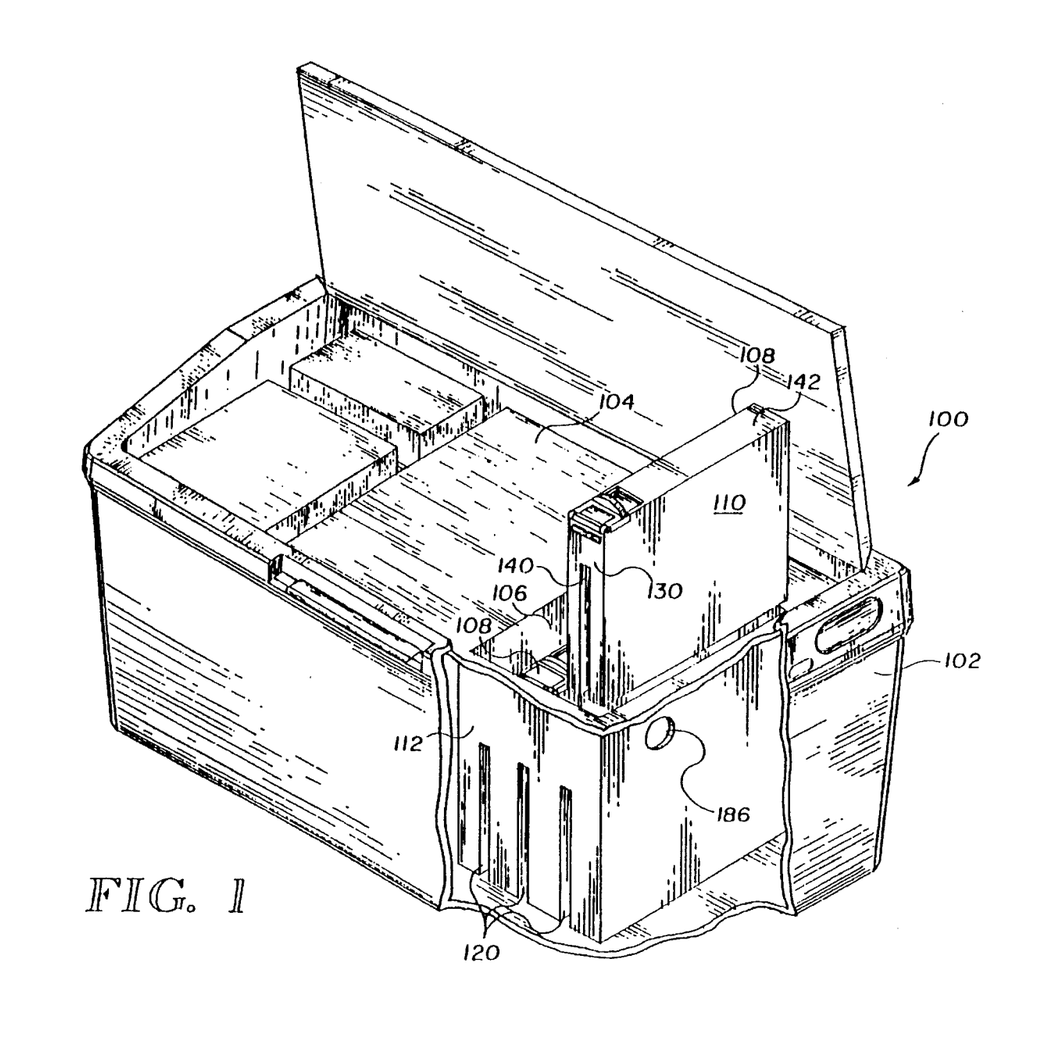
FIG. 1 is an isometric front view of a portable medical electronic device of the present invention having a socket and showing a module inserted therein.

A portable medical electronic device 100, such as a defibrillator or medical monitor, is shown in FIG. 1 as having a housing 102 enclosing medical electronic circuitry (not shown). A receiving socket 106 formed in a top side 104 of the housing 102 is sized to receive one or more feature modules 108. The module 108 includes a case 110 enclosing expanded functional circuitry (not shown), such as blood pressure monitoring or data recordation circuitry. When the module 108 is inserted into the socket 106, the expanded functional circuitry electrically couples with the medical electronic circuit enclosed within the housing 102. In such manner, the functionality of the portable medical electronic device 100 may be altered or expanded by inserting one or more modules 108 into the socket 106.

Figure 2:
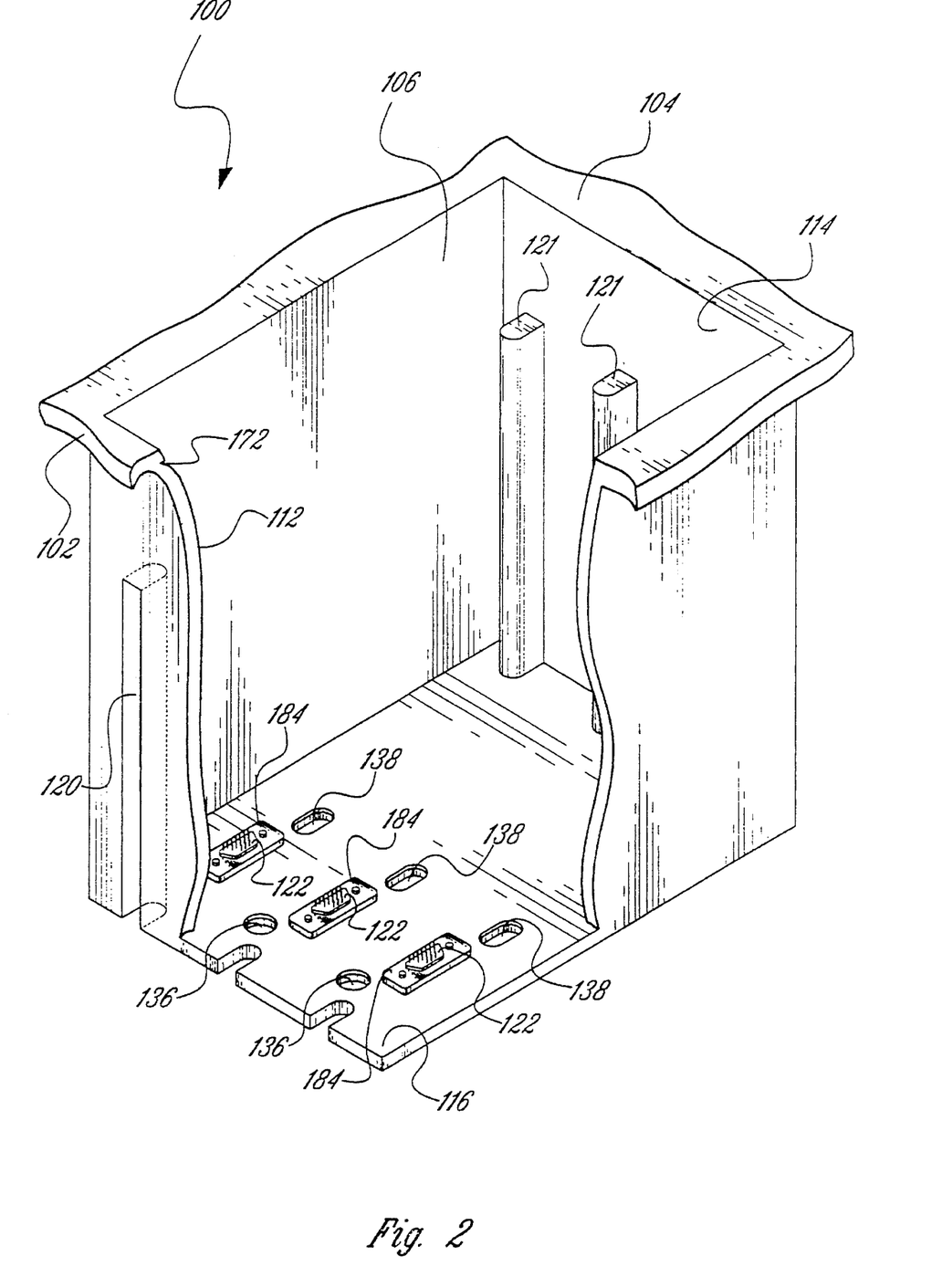
FIG. 2 is an enlarged, fragmentary, isometric view of the socket of FIG. 1.
Figure 3:
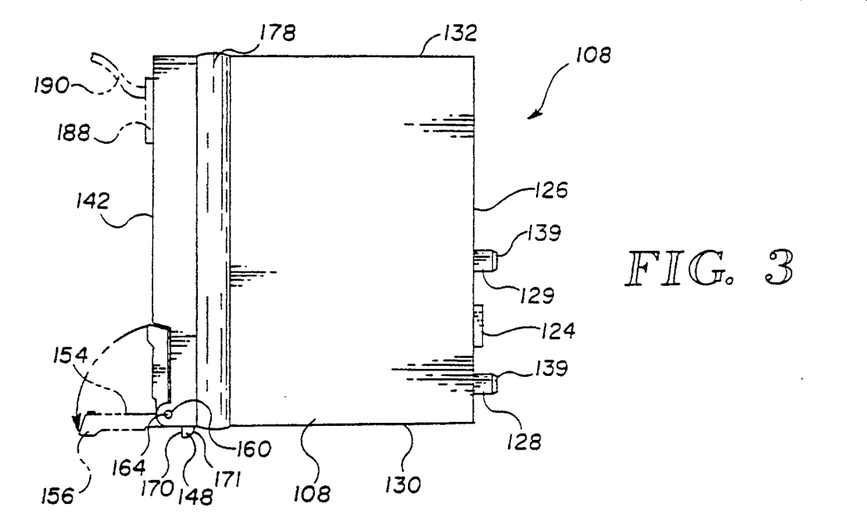
FIG. 3 is a fight side elevational view of the module of FIG. 1.
Figure 4:
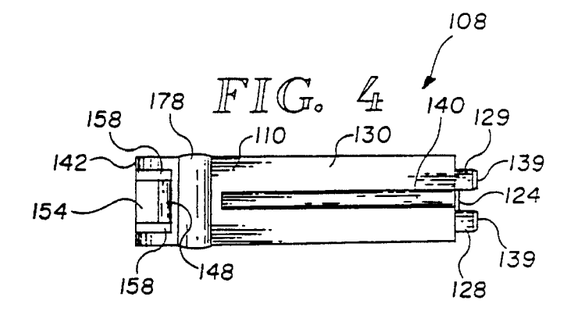
FIG. 4 is a front elevational view of the module of FIG. 1.

Referring to FIG. 2, the socket 106 is defined by a front sidewall 112, a rear sidewall 114, a bottom wall 116, and left and right sidewalls, forming an approximately rectangular-shaped opening in the top side 104 of the housing 102. Three front ribs 120 project rearward from the front sidewall 112, each rib 120 extending from the bottom wall 116 toward the top side of the housing 104. The three front ribs 120 projecting from the front sidewall 112 are approximately equidistant from each other. In a like manner, the rear sidewall 114 has three equidistant rear ribs 121 projecting forward therefrom and extending from the bottom wall 116 toward the top side 104.

Referring also now to FIGS. 3–6, case 110 of the module 108 has a bottom side 126, a front side 130, a rear side 132, a top side 142 and leer and right sides. The socket 106 may receive one or more modules having at least three different widths. The module 108 depicted and generally described herein is a single width module. The socket 106 depicted and described herein is capable of accepting a module at least three times wider than the single width module 108. A module having twice the width of the module 108 may also be inserted into the socket 106. In the single width module 108, the case 110 is able to accommodate at least two printed circuit boards therein containing the expanded functional circuitry for that particular module. Modules having greater widths can accommodate greater numbers of printed circuit boards and therefore contain a greater amount of expanded functional circuitry. While the single width module 108 is discussed herein, the discussion applies generally to all other widths of modules.

The front and rear sides 130 and 132 of the case 110 each have a channel 140 formed therein extending from the bottom side 126 of the case to the top side 142 of the case. The front and rear channels 140 are sized to receive one pair of front or rear ribs 120 and 121, respectively. Each channel 140 preferably extends approximately 2.9 inches from the bottom side 126 toward the top side 142 of the case 110. The front and rear sides 130 and 132, respectively, of the case 110 are preferably separated from each other by a distance of approximately 4.4 inches. Each channel 140 may extend inward with respect to the case 110 by a distance of approximately 0.27 inch. With these dimensions, each front rib 120 is separated from its corresponding rear rib 121 by approximately 4 inches.

Figure 5:
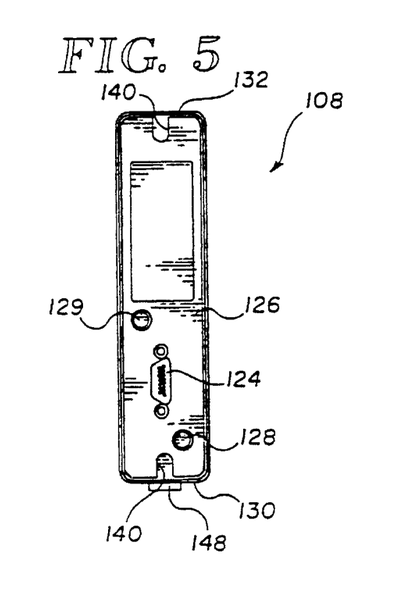
FIG. 5 is a bottom plan view of the module of FIG. 1.

A housing electrical connector 122 projects upward from the bottom wall 116 of the socket 106 proximate to each front rib 120. A case electrical connector 124 protrudes from a bottom side 126 of the case 110 of the module 108. The housing electrical connector 122 and the case electrical connector 124 are selected from known connectors to securely electrically interconnect the module 108 and the electronic device 100 and are each preferably 15-pin connectors.

From and rear guide pins 128 and 129, respectively, project downward from the bottom side 126 of the module 108 on opposing sides of the case electrical connector 124. The front guide pin 128 projects from the bottom side 126 of the case 110 between the front side 130 of the case 110 and the case electrical connector 124. The rear guide pin 129 projects from the bottom side 126 of the case 110 between the rear side 132 and the case electrical connector 124. The center of the front guide pin 128 is preferably 0.7 inch from the center of the case electrical connector 124 and 0.5 inch from the front side 130 of the case 110. The centers of the front and rear guide pins 128 and 129 are preferably 1.5 inches apart in the front-to-rear direction. In the left-to-right direction, the front and rear guide pins 128 and 129 are preferably 0.5 inch apart. Generally, as used herein, all measurements are with respect to a centerline down the appropriate side or surface.

The front and rear guide pins 128 and 129 project below the bottom side 126 of the case 110 by approximately 0.28 inch, projecting a substantial distance beyond that of the case electrical connector 124 (which projects downward approximately 0.1 inch). By projecting proximate to and beyond the distance of the case electrical connector 124, the from and rear guide pins 128 and 129 protect the case electrical connector 124 from damaging impact should the module 108 be dropped onto its bottom side 126.

A round hole 136 is formed in the bottom wall 116 of the socket 106, between each front rib 120 and each housing electrical connector 122, and is positioned and sized to receive the front guide pin 128 when the module 108 is inserted into the socket 106. Similarly, an oblong hole 138 is formed in the bottom wall 116 between each housing electrical connector 122 and each rear rib 121, and is positioned and sized to receive the rear guide pin 129. The round and oblong holes 136 and 138 are thus separated from each other by approximately 1.5 inches. Each oblong hole 138 has a slight oblong shape extending in a front-to-rear direction between each pair of front and rear ribs 120 and 121, respectively, for reasons that will be explained below.

The front and rear guide pins 128 and 129 preferably have chamfered ends 139, and the round and oblong holes 136 and 138 have mating tapering bottoms to receive the chamfered ends 139. The chamfered ends 139 of the front and rear guide pins 128 and 129 help guide the pins into their respective holes 136 and 138 when the modulate 108 is inserted into the socket 106. The guide pins 128 and 129 and the holes 136 and 138 are positioned off center so that the module 108 may be received by the socket 106 in only one orientation, thus preventing a user from fully inserting the module in the opposite orientation in which the housing electrical connector 122 and the case electrical connector 124 do not interconnect.

Figure 7:
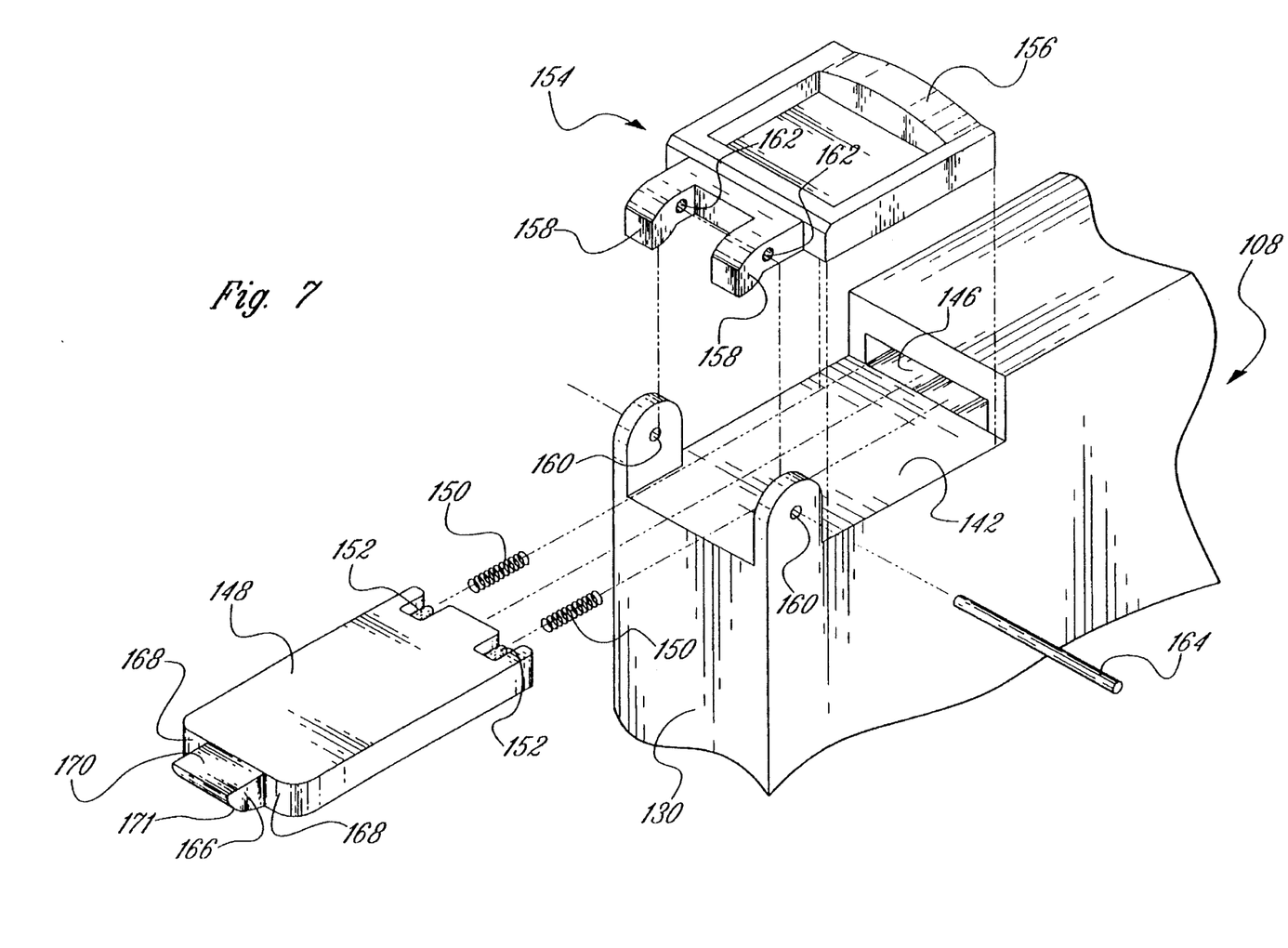
FIG. 7 is an enlarged, exploded isometric view of a latching assembly of the module of FIG. 1.

Referring to FIG. 7, a latching assembly for retaining the module 108 in the socket 106 is shown. While one such latching assembly is shown and described herein, the present invention may use a variety of latching assemblies to releasably retain the module 108 in the socket 106. As shown in FIG. 7, a bolt slot 146 formed in the front side 130 of the case 110 proximate to the top side 142 slidably receives latch bolt 148. A pair of springs 150 are retained on a pair of spring pins 152 formed on and projecting rearward of the latch bolt 148. The springs 150 rest against a rear wall of the bolt slot 146 and bias the latch bolt 148 forward.

A lever 154 retained on the top side 142 of the case 110 includes a gripping portion 156 and a pair of left and right camming arms 158. A pair of left and fight retaining holes 160 formed in the top side 142 of the case 110, and a pair of left and right pin holes 162 formed in the lever 154 between the camming arms 158 and the gripping portion 156, receive a pivot pin 164 to retain the lever 154 against the top side of the case.

When the lever 154 is retained at the top side 142 of the case 110, the camming arms 158 extend downward and between a forward extending head 166 formed in the latch bolt 148. The head 166 has a flat top surface 170 and a curved bottom surface 171. The left and right camming arms 168 rest against left and right shoulders 168 extending from left and right sides of the head 166 of the latch bolt 148. The springs 150 bias the latch bolt 148 forward, biasing the left and right shoulders 168 against the left and right camming arms 158. The left and right camming arms 158 are shaped so as to exert a pivot force on the lever 154 about the pin 164 when the left and right shoulders 168 exert a forward force against the camming arms. This pivot force causes the gripping portion 156 to pivot downward and rest against the top side 142 of the case 110 in a rest position. In the rest position, the head 166 projects forward between the left and fight camming arms 156 and extends forward of the front side 130 of the case 110.

When the module 108 is fully received by the socket 106, the flat top surface 170 of the head 166 is adjacent to and below a ledge 172 (FIG. 2) formed in the housing 102 along an upper portion of the front sidewall 112 transverse to the front ribs 120. The ledge 172 projects rearward into the socket 106 and is positioned to releasably receive the flat top surface 170 of the head 166 when the module 108 is positioned in the socket. When so received, upward movement of the module 108 is restricted by the flat top surface 170 of the head 166 contacting the underside of the ledge 172. Downward movement of the module 108 is restricted by the bottom wall 116 of the socket 106.

A user may remove the module 108 from the socket 106 by seizing the gripping portion 156 and pivoting it upward. As the gripping portion 156 pivots upward about the pin 164, the left and fight camming arms 158 pivot rearward and against the left and fight shoulders 168 of the latch bolt 148. As the left and right camming arms 158 pivot rearward, the latch bolt 148 slides rearward in the bolt slot 146, compressing the springs 150. As the latch bolt 148 slides rearward, the head 166 retracts to an unlatched position, away from contact with the ledge 172. The gripping portion 156 of the lever 154 is preferably ring-shaped or has a sufficient frictional gripping surface to allow a user to pull the module 108 from the socket 106 once the head 166 is retracted from engagement with the ledge 172.

The lever 154 and the case connector 124 are positioned proximate to the front side of the case 130 so that when the module 108 is pulled from the socket 106 by means of the lever 154, a substantially upward force is exerted on the case electrical connector 124 as this connector pulls away from interconnection with the housing electrical connector 122. This substantially upward force minimizes any damaging torquing forces which may be placed on the case or housing electrical connectors 122 and 124 when the module 108 is removed from the socket 106. Similarly, a substantially upward force is exerted on the from and rear guide pins 128 and 129 as they are pulled upward and out of the round and oblong holes 136 and 138. This upward force exerts minimal torquing force on the pins 128 which otherwise could frictionally bind the pins 128 in the holes 136, 138, thereby inhibiting removal of the module 108 from the socket 106.

To reinsert the module 108, the user aligns the channels 140 in the from and rear sides 130 and 132 of the case 110 with the from and rear ribs 120 and 121, respectively, in the socket 106 and slides the module 108 downward. The ribs and channels provide an initial course adjustment to guide the module 108 into the socket 106 arid align the front and rear guide pins 128 and 129 with the round and oblong holes 136 and 138, respectively. Once the pins 128, 129 have been inserted into the holes 136, 138, respectively, the pins 128, 129 provide fine positioning to guide the case electrical connector 124 into the housing electrical connector 122.

The front guide pin 128, when received by the round hole 136, aligns the module 108 along a first axis, but permits rotation of the module. The rear guide pin 129, when received by the oblong hole 138, aligns the module 108 along a second axis perpendicular to the first axis, and prevents rotation of the module. The first and second axes are approximately parallel with the bottom wall 116. The case electrical connector 124 is in linear alignment with the grooves 140 with respect to the bottom side 126 of the case 110, and are preferably aligned along the centerline of the bottom side 126. The front and rear guide pins 128 and 129 are offset with respect to this line. Specifically, the front and rear guide pins 128 and 129 are linearly aligned with the case electrical connector 124 and diagonally offset from the centerline, with the case electrical connector 124 being at the point of intersection between the centerline and the line intersecting the pins and the connector. By positioning the pins 128, 129 diagonally offset from the centerline of the module 108, the module is prohibited from rocking about a third axis perpendicular to the first and second axes.

The longer sides of the oblong hole 138 (i.e., the left and fight sides) contact opposing sides of the rear pin 129. The oblong hole has an oblong shape, and the front and rear pins 128 and 129 are placed close together relative to the size of the module 108, to permit a small degree of variability when inserting the module. This variability allows the module 108 to be adjusted or moved a small degree in order to align and couple the case electrical connector 124 with the housing electrical connector 122. This variability also compensates for variances in manufacturing. Overall, the interplay in tolerances between the front and rear ribs 120 and 121 with the channels 140, and the front and rear guide pins 128 and 129 with the round and oblong holes 136 and 138, all respectively, allow the module 108 to be easily inserted into the socket 106 and allow precise interconnection between the case and housing electrical connectors 124 and 122.

The curved bottom surface 171 of the head 166 is shaped such that when the head 166 contacts an upper edge of the ledge 172 upon insertion of the module 108, a downward force applied to the module 108 causes the latch bolt 166 to slide rearward and away from the ledge 172 as the curved bottom surface slides against the upper edge. A user need not lift the gripping portion 156 of the lever 154 to retract the latch bolt 148 when inserting the module 108 into the socket 106.

An elastic seal 178 extends about the front side 130, the rear side 132, and the left and right sides of the case 110 proximate to the top side 142 and below the latch bolt 148. When three of the single width modules 108 are inserted into the socket 106, the elastic seals 178 about the modules contact the front sidewall 112, the rear sidewall 113, the left and right sidewalls, and each other to thereby form an environmental seal whereby particles or contaminants are inhibited from penetrating into the socket 106. Additionally, the elastic seals 178 provide shock-absorbing benefits to allow the modules 108 to withstand impact shocks imposed on them directly or through the device 100. If an insufficient number or numbers of modules 108 are inserted into the socket 106 to fill the socket, a spacer (not shown) of the appropriate width having a similar elastic seal 178 about its exterior may be inserted into the empty slot or slots to ensure environmental integrity and absorb impact shock.

Elastomeric gaskets 184 are secured between each housing electrical connector 122 and the bottom wall 116 of the housing 102. The case 110 is similarly sealed to inhibit the penetration of fluids into the interior of the module 108. The bolt slot 146 is sealed from the interior of the case 110. An elastomeric gasket (not shown), similar to the elastomeric gasket 184, is retained about the case electrical connector 124 and the bottom side 126.

Figure 6:
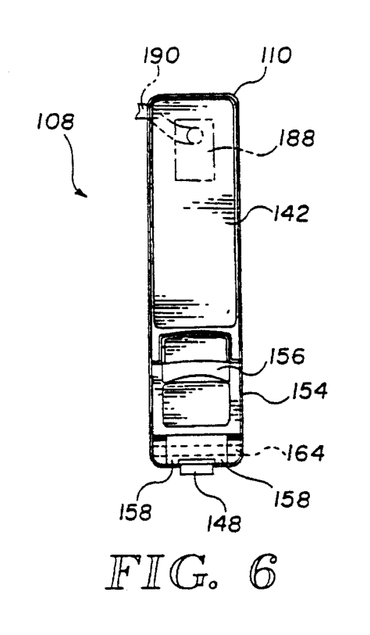
FIG. 6 is a top plan view of the module of FIG. 1.

The top side 142 of the case 110 is designed to accommodate various connectors or ports allowing wires, cables, tubing or other transmission conduits 190 to be coupled between the module 108 and the exterior of the device 100. Specifically, the device 100 includes a port 186 adjacent to the right sidewall of the socket 106, as shown in FIG. 1. The port 186 is of sufficient size to accommodate the various diameters of various transmission conduits 190 extending from the upper surface of the modules 108 as shown in FIG. 6. An area of the top side 142 of the case 110 is provided to accommodate a large variety of connectors, such as an external connector 188 shown in dashed lines in FIG. 6. For example, the module 108 can be a heart rate monitor wherein an electrical external connector 188 is provided in the area of the top side 142 to which wires 190 for electrodes may be coupled. Such wires can then be positioned through the port 186 to the exterior of the device 100. Alternatively, the module 108 can be a blood pressure monitor whereby the area of the top side 142 accommodates a pneumatic tube external connector 188. A pneumatic tube 190 coupled from the connector 188 can extend therefrom to the exterior of the device 100, through the port 186, to a blood pressure monitoring cuff.

The present invention describes the portable medical electronic device 100 which allows the functions of the device to be readily changed or upgraded through the use of the modules 108. The modules 108 avoid impact shock and other environmental hazards inherent in a portable electronic device 100, yet allow ready insertion or removal of the module by using a two-step method of interconnecting the modulate to the electronic device. In the first step, when the module 108 is inserted into the socket 106, the front and rear channels 140 and front and rear ribs 120 and 121 align the front and rear guide pins 128 and 129 with the round and oblong holes 136 and 138, respectively. In a second step, the front and rear guide pins 128 and 129 guide the case electrical connector 124 into the housing electrical connector 122 when the pins are received by the holes 136 and 138, respectively. Thereafter, the case and housing electrical connectors 124 and 122 are designed to further align themselves to electrically intercouple (e.g., having chamfered mechanical features and electrical sockets). Concurrently, the latching assembly allows the latch bolt 148 to extend into the bolt slot 146 and thereafter project outwardly therefrom to engage the ledge 172, releasably retaining the module 108 in the socket 106.

No known system provides such a multi-step method of interconnecting a module with an electronic device. Interconnecting a module with an electronic device using ribs and channels alone, or pins and holes alone, is insufficient to provide both electrical interconnection capable of withstanding impact shock and ready insertion/removal of the module from the device.

The front and rear pins 128 and 129 of the module 108 provide multiple benefits. The front and rear guide pins 128 and 129 align the module 108 along first and second perpendicular axes to prevent the module from shifting and rotating. The pins 128, 129 are also diagonally offset from the centerline of the module 108 to prohibit the module from rocking about the third perpendicular axis. The front and rear guide pins 128 and 129 protect the case electrical connector 124 by extending downward at a distance greater than that of the case electrical connector and by being positioned on opposing sides of the case electrical connector. The chamfered end 139 of each pin allows the pin to be readily and securely positioned within its respective hole.

Although a specific embodiment of the invention has been described for purposes of illustration, various modifications may be made without departing from the spirit and scope of the invention, as is known by those skilled in the relevant art. Accordingly, the invention is not limited by the disclosure, but instead the scope is to be determined entirely by reference to the following claims.

I claim:

1. In a portable medical electronic device having a medical electronic circuit, a modular system for permitting additional functional modules having electrical components to electrically couple to the medical electronic circuit comprising:

a module including a case having top, bottom, front and rear sides, the front and rear sides of the case each having a channel formed therein extending from the bottom of the case toward the top of the case, a first electrical connector projecting below the bottom of the case a first distance proximate to the front side of the case, and a pair of guide pins extending below the bottom of the case a second distance, proximate to, and on opposing sides of, the first electrical connector, the second distance being greater than the first distance, the guide pins being separated by a distance of approximately 1.5 inches, and the module being further defined by a rear channel formed therein;

a housing having top, bottom, front and rear sides and enclosing the medical electronic circuit, the housing having a socket for releasably receiving the module, the socket defined by a bottom wall and a sidewall of the housing, the sidewall having a first rib projecting therefrom, the first rib extending from the bottom wall toward the top of the housing and sized to be received by the channel formed in the front side of the case, the bottom wall having first and second holes formed therein proximate to the first rib, the first and second holes for receiving the pair of guide pins and being separated by a distance of approximately 1.5 inches; and, a second electrical connector electrically coupled to the medical electronic circuit and positioned within the bottom wall of the housing and retained by the housing between the first and second holes, the second electrical connector for electrically coupling with the first electrical connector when the module is inserted into the socket.

2. In a portable medical electronic device having a medical electronic circuit, a modular system for permitting additional functional modules having electrical components to electrically couple to the medical electronic circuit comprising:

a module including a case having top, bottom, front and rear sides, the front and rear sides of the case each having a channel formed therein extending from the bottom of the case toward the top of the case, a first electrical connector projecting below the bottom of the case a first distance proximate to the front side of the case, and a pair of guide pins extending below the bottom of the case a second distance, proximate to, and on opposing sides of, the first electrical connector, the second distance being greater than the first distance, the module being further defined by a rear channel formed therein:

a housing having top, bottom, front and rear sides and enclosing the medical electronic circuit, the housing having a socket for releasably receiving the module, the socket defined by a bottom wall and a sidewall of the housing, the sidewall having a first rib projecting therefrom, the first rib extending from the bottom wall toward the top of the housing and sized to be received by the channel formed in the front side of the case, the bottom wall having first and second holes formed therein proximate to the first rib, the first and second holes for receiving the pair of guide pins, the socket being further defined by a rear sidewall, the rear sidewall having a second rib extending therefrom, the second rib sized to be received by the rear channel and, a second electrical connector electrically coupled to the medical electronic circuit and positioned within the bottom wall of the housing and retained by the housing between the first and second holes, the second electrical connector for electrically coupling with the first electrical connector when the module is inserted into the socket.

3. The modular system of claim 2 wherein the first hole has a circular shape and the second hole has an oblong shape, the oblong shape extending in a direction between the first rib and the second rib.

4. The modular system of claim 2 wherein the first and second ribs are separated from each other by a distance of approximately 4 inches.

5. In a portable medical electronic device having a medical electronic circuit enclosed by a housing, the housing having top, bottom, front and rear sides and a socket formed in the top side, the socket defined by a bottom wall and a sidewall of the housing, the sidewall having a first rib projecting therefrom, the first rib extending from the bottom wall toward the top of the housing, the bottom wall having first and second holes formed therein, proximate to the first rib, and a first electrical connector electrically coupled to the medical electronic circuit and positioned within the bottom wall of the housing and retained by the housing between the first and second holes, a module for permitting additional electrical components to electrically couple to the medical electronic circuit comprising:

a case having top, bottom, front and rear sides, the front side of the case having a channel formed therein extending along the front side of the case from the bottom of the case toward the top of the case and sized to receive the first rib;

a second electrical connector projecting below the bottom of the case a first distance, proximate to the front side of the case;

a pair of guide pins extending below the bottom of the case a second distance, proximate to, and on opposing sides of, the second electrical connector, the guide pins sized to be received by the first and second holes, the second distance being, approximately 0.28 inch and being greater than the first distance;

a latch member extending from the front side of the case proximate to the top of the case, the latch member for movement between an extended latched position and a retracted unlatched position; and an actuator assembly retained by the case and adapted to move the latch member between the extended latched position and the retracted unlatched position.

6. In a portable medical electronic device having a medical electronic circuit enclosed by a housing, the housing having top, bottom, front and rear sides and a socket formed in the top side, the socket defined by a bottom wall and a sidewall of the housing, the sidewall having a first rib projecting therefrom, the first rib extending from the bottom wall toward the top of the housing, the bottom wall having first and second holes formed therein, proximate to the first rib, and a first electrical connector electrically coupled to the medical electronic circuit and positioned within the bottom wall of the housing and retained by the housing between the first and second holes, a module for permitting additional electrical components to electrically couple to the medical electronic circuit comprising:

a case having top, bottom, front and rear sides, the front side of the case having a channel formed therein extending along the front side of the case from the bottom of the case toward the top of the case and sized to receive the first rib, wherein the front and rear sides of the case are separated from each other by a distance of approximately 4.4 inches;

a second electrical connector projecting below the bottom of the case a first distance, proximate to the front side of the case;

a pair of guide pins extending below the bottom of the case a second distance, proximate to, and on opposing sides of, the second electrical connector, the guide pins sized to be received by the first and second holes, the second distance being greater than the first distance;

a latch member extending from the front side of the case proximate to the top of the case, the latch member for movement between an extended latched position and a retracted unlatched position; and an actuator assembly retained by the case and adapted to move the latch member between the extended latched position and the retracted unlatched position.

7. In a portable medical electronic device having a medical electronic circuit enclosed by a housing, the housing having top, bottom, front and rear sides and a socket formed in the top side, the socket defined by a bottom wall and a sidewall of the housing, the sidewall having a first rib projecting therefrom, the first rib extending from the bottom wall toward the top of the housing, the bottom wall having first and second holes formed therein, proximate to the first rib, and a first electrical connector electrically coupled to the medical electronic circuit and positioned within the bottom wall of the housing and retained by the housing between the first and second holes, a module for permitting additional electrical components to electrically couple to the medical electronic circuit comprising:

a case having top, bottom, front and rear sides, the front side of the case having a channel formed therein extending along the front side of the case from the bottom of the case toward the top of the case and sized to receive the first rib, wherein the channel extends a distance of approximately 2.9 inches from the bottom of the case toward the top of the case and extends into the case approximately 0.26 inch;

a second electrical connector projecting below the bottom of the case a first distance, proximate to the front side of the case;

a pair of guide pins extending below the bottom of the case a second distance, proximate to, and on opposing sides of, the second electrical connector, the guide pins sized to be received by the first and second holes, the second distance being greater than the first distance;

a latch member extending from the front side of the case proximate to the top of the case, the latch member for movement between an extended latched position and a retracted unlatched position; and an actuator assembly retained by the case and adapted to move the latch member between the extended latched position and the retracted unlatched position.

8. In a portable medical electronic device having a medical electronic circuit enclosed by a housing, the housing having top, bottom, front and rear sides and a socket formed in the top side, the socket defined by a bottom wall and a sidewall of the housing, the sidewall having a first rib projecting therefrom, the first rib extending from the bottom wall toward the top of the housing, the bottom wall having first and second holes formed therein, proximate to the first rib, and a first electrical connector electrically coupled to the medical electronic circuit and positioned within the bottom wall of the housing and retained by the housing between the first and second holes, a module for permitting additional electrical components to electrically couple to the medical electronic circuit comprising:

a case having top, bottom, front and rear sides, the front side of the case having a channel formed therein extending along the front side of the case from the bottom of the case toward the top of the case and sized to receive the first rib;

a second electrical connector projecting below the bottom of the case a first distance, proximate to the front side of the case;

a pair of guide pins extending below the bottom of the case a second distance, proximate to, and on opposing sides of, the second electrical connector, the guide pins sized to be received by the first and second holes, the second distance being greater than the first distance, wherein the pair of guide pins are separated from each other by a distance of approximately 1.5 inches;

a latch member extending from the front side of the case proximate to the top of the case, the latch member for movement between an extended latched position and a retracted unlatched position; and an actuator assembly retained by the case and adapted to move the latch member between the extended latched position and the retracted unlatched position.

9. In a portable medical electronic device having a medical electronic circuit enclosed by a housing, the housing having top, bottom, front and rear sides and a socket formed in the top side, the socket defined by a bottom wall and a sidewall of the housing, the sidewall having a first rib projecting therefrom, the first rib extending from the bottom wall toward the top of the housing, the bottom wall having first and second holes formed therein, proximate to the first rib, and a first electrical connector electrically coupled to the medical electronic circuit and positioned within the bottom wall of the housing and retained by the housing between the first and second holes, a module for permitting additional electrical components to electrically couple to the medical electronic circuit comprising:

a case having top, bottom, front and rear sides, the front side of the case having a channel formed therein extending along the front side of the case from the bottom of the case toward the top of the case and sized to receive the first rib;

a second electrical connector projecting below the bottom of the case a first distance, proximate to the front side of the case;

a pair of guide pins extending below the bottom of the case a second distance, proximate to, and on opposing sides of, the second electrical connector, the guide pins sized to be received by the first and second holes, the second distance being greater than the first distance, and the pair of guide pins each having a chamfered end;

a latch member extending from the front side of the case proximate to the top of the case, the latch member for movement between an extended latched position and a retracted unlatched position; and an actuator assembly retained by the case and adapted to move the latch member between the extended latched position and the retracted unlatched position.

10. In a medical electronic device having a medical electronic circuit enclosed by a housing, the housing having a top side and a socket formed in the top side, the socket defined by a bottom wall and front and rear sidewalls of the housing, the front and rear sidewalls having front and rear ribs projecting therefrom, respectively, the front and rear ribs extending from the bottom wall toward the top side of the housing, the bottom wall having first and second holes formed therein, proximate to the front rib, and a first electrical connector electrically coupled to the medical electronic circuit and positioned within the bottom wall of the housing and retained by the housing between the first and second holes, a module for permitting additional electrical components to electrically couple to the medical electronic circuit comprising:

a case having top, bottom, front and rear sides, the front and rear sides of the case having a channel formed therein extending along the front and rear sides of the case from the bottom, of the case toward the top of the case and sized to receive the front and rear ribs, respectively, the front and rear sides of the case being separated from each other by a distance of approximately 4.4 inches: and a second electrical connector projecting below the bottom of the case a first distance, proximate to the front side of the case, the front and rear channels and the second electrical connector linearly aligned with respect to the bottom side of the case.

11. In a medical electronic device having a medical electronic circuit enclosed by a housing, the housing having a top side and a socket formed in the top side, the socket defined by a bottom wall and front and rear sidewalls of the housing, the front and rear sidewalls having front and rear ribs projecting therefrom, respectively, the front and rear ribs extending from the bottom wall toward the top side of the housing, the bottom wall having first and second holes formed therein, proximate to the front rib, and a first electrical connector electrically coupled to the medical electronic circuit and positioned within the bottom wall of the housing and retained by the housing between the first and second holes, a module for permitting additional electrical components to electrically couple to the medical electronic circuit comprising:

a case having top, bottom, front and rear sides, the front and rear sides of the case having a channel formed therein extending along the front and rear sides of the case from the bottom of the case toward the top of the case and sized to receive the front and rear ribs, respectively, wherein the front and rear channels each extend a distance of approximately 2.9 inches from the bottom of the case to the top of the case, and extend into the case approximately 0.26 inch; and a second electrical connector projecting below the bottom of the case a first distance, proximate to the front side of the case, the front and rear channels and the second electrical connector linearly aligned with respect to the bottom side of the case.

12. In a medical electronic device having a medical electronic circuit enclosed by a housing, the housing having a top side and a socket formed in the top side, the socket defined by a bottom wall and front and rear sidewalls of the housing, the front and rear sidewalls having front and rear ribs projecting therefrom, respectively, the front and rear ribs extending from the bottom wall toward the top side of the housing, the bottom wall having first and second holes formed therein, proximate to the front rib, and a first electrical connector electrically coupled to the medical electronic circuit and positioned within the bottom wall of the housing and retained by the housing between the first and second holes, a module for permitting additional electrical components to electrically couple to the medical electronic circuit comprising:

a case having top, bottom, front and rear sides, the front and rear sides of the case having a channel formed therein extending along the front and rear sides of the case from the bottom of the case toward the top of the case and sized to receive the front and rear ribs, respectively;

a second electrical connector projecting below the bottom of the case a first distance, proximate to the front side of the case, the front and rear channels and the second electrical connector linearly aligned with respect to the bottom side of the case; and a pair of pins extending below the bottom of the case a second distance, proximate to, and on opposing sides of the second electrical connector, the guide pins sized to be received by the first and second holes, and each pin having a chamfered end.

* * * * *